United States Patent [19]
Jordan

[11] Patent Number: 5,885,617
[45] Date of Patent: Mar. 23, 1999

[54] MOISTURE BARRIER FILM COATING COMPOSITION, METHOD, AND COATED FORM

[75] Inventor: Martin Philip Jordan, Orpington, England

[73] Assignee: BPSI Holdings, Inc., Wilmington, Del.

[21] Appl. No.: 466,939

[22] Filed: Jun. 6, 1995

[30] Foreign Application Priority Data

Jul. 12, 1994 [GB] United Kingdom .................. 9414045

[51] Int. Cl.⁶ .............................. A61K 9/32; A61K 9/34; A61K 9/36
[52] U.S. Cl. ........................ 424/474; 424/461; 424/462; 424/463; 424/476; 424/480; 424/481; 424/482; 424/493; 424/494; 424/496; 424/497; 424/498; 514/770; 514/772.2; 514/778; 514/779; 514/781; 514/782; 514/786; 106/210.1; 106/215.1; 106/243
[58] Field of Search ..................................... 424/474, 482, 424/497, 498, 461, 462, 479, 480, 481, 493, 494, 496, 476

[56] References Cited

U.S. PATENT DOCUMENTS

| | | | |
|---|---|---|---|
| 3,997,674 | 12/1976 | Ukai et al. ................................. | 426/90 |
| 4,341,563 | 7/1982 | Kurihara .................................. | 106/171 |
| 5,206,030 | 4/1993 | Wheatley ................................. | 424/490 |
| 5,393,333 | 2/1995 | Trouve ..................................... | 106/149 |
| 5,411,746 | 5/1995 | Signorino ................................. | 424/464 |

*Primary Examiner*—Thurman K. Page
*Assistant Examiner*—James M. Spear
*Attorney, Agent, or Firm*—John F. A. Earley; John F. A. Earley, III; Harding, Earley, Follmer & Frailey

[57] ABSTRACT

A dry moisture barrier film coating composition for forming a moisture barrier film coating for pharmaceutical tablets and the like comprises polyvinyl alcohol, soya lecithin, and optionally a flow aid, a colorant, and/or a suspending agent. A liquid coating solution or dispersion for forming a moisture barrier film coating for pharmaceutical tablets and the like comprises polyvinyl alcohol, soya lecithin, water, and optionally a flow aid, a colorant, and/or a suspending agent. A method of coating pharmaceutical tablets and the like with a moisture barrier film coating comprises forming a liquid coating solution or dispersion for forming a moisture barrier film coating for pharmaceutical tablets and the like comprising polyvinyl alcohol, soya lecithin, water, and optionally a flow aid, a colorant, and/or a suspending agent, applying the coating solution or dispersion onto the tablets to form a film coating on the tablets, and drying the film coating on the tablets.

33 Claims, No Drawings

MOISTURE BARRIER FILM COATING COMPOSITION, METHOD, AND COATED FORM

BACKGROUND OF THE INVENTION

1. Field of the Invention

This invention is in the field of coating of substrates like pharmaceutical tablets, and it is specifically concerned with coating such substrates with a coating that acts as a moisture barrier.

2. Description of the Prior Art

Many medicinal substances and the dosage forms into which they are made undergo degradation during storage due to contact with moisture which has been absorbed from the atmosphere. To combat this degradation, it is frequently necessary for such moisture sensitive dosage forms to be packed in special containers to limit the exposure of the dosage forms to the atmosphere.

In territories where the climate is very humid, specialized packaging does not provide a totally satisfactory answer to moisture degradation.

Elimination of the need for the special packaging, or augmentation of the moisture protection provided by such packaging, may be achieved in the case of solid dosage forms, such as tablets, capsules and granules, by coating with materials which reduce the rate at which the dosage form absorbs atmospheric moisture. Moisture barrier coatings of this type have been employed previously. The traditional means of providing the moisture barrier characteristics required for moisture barrier coatings has been by the use of polymers which are soluble in organic solvents or are relatively insoluble in water. The disadvantages of this approach are 1) the need to use either organic solvents or difficult aqueous polymer dispersion techniques to apply these water-insoluble polymer materials, and 2) the reduced Aqueous solubility of the coating leading to prolonged disintegration time of the dosage form in the body when ingested, with consequent delayed or reduced activity of the medicinal substance in the tablet.

The use of the polymer polyvinyl alcohol, PVA, as a moisture barrier coating has been previously suggested. However, practical usage has been inhibited by the stickiness of grades of the polymer which have a fast enough rate of going into solution in water to make a dispersion to render them economical to use in making the coating. A further problem with the use of PVA is in identifying or selecting a plasticizer which does not compromise the moisture barrier properties of the final coating.

SUMMARY OF THE INVENTION

A dry powder moisture barrier coating composition is made to form a moisture barrier film coating for pharmaceutical tablets and the like, which comprises polyvinyl alcohol in combination with soya lecithin, together with, none, one or more of the following components which enhances the desirable coating characteristics of the resulting film coating: a flow aid, a colorant, and a suspending agent.

A method of making the moisture barrier film coating powder composition of the invention comprises the steps of mixing polyvinyl alcohol with soya lecithin and optionally with one or more of the following components, until a dry homogenous powder mixture is produced: a flow aid, a colorant, and a suspending agent. Preferably, the mixture of polyvinyl alcohol and soya lecithin, or the mixture of polyvinyl alcohol and soya lecithin and any of the following components, if any of the following components is to be included in the coating composition, is milled: a flow aid, a colorant, and a suspending agent. The resulting dry powder coating composition is readily soluble or dispersible in cold water to form a liquid coating solution or dispersion that is ready to use within 45 minutes.

Another method of making a dry edible film coating composition of the invention comprises producing a mixture of the ingredients processed into a granular form to form a granular coating composition by using any of the following methods: wet massing, fluid bed granulation, spray granulation and dry compaction, roller compaction or slugging.

The invention also includes a liquid coating solution or dispersion for forming a moisture barrier film coating which comprises polyvinyl alcohol, soya lecithin, an optional flow aid, an optional colorant, and an optional suspending agent mixed into water.

The method of making the liquid coating dispersion of the invention comprises dispersing the dry powder coating composition, the granular coating composition, or the individual ingredients of the coating composition separately, into hot or cold water, and/or milling and/or stirring until a homogenous mixture of a desired correct viscosity is produced.

The film former of the coating is the polyvinyl alcohol, which may be GOHSENOL polyvinyl alcohol made by NIPPON GOHSEI, for example.

Excellent moisture barrier properties are obtained when hot water soluble grades of PVA are used in the inventive coating, but use of such grades requires that the water of the liquid coating dispersion be heated. The coatings of the invention may use cold water soluble grades of PVA to provide moisture barrier protection, but they provide less moisture barrier protection than that provided by the inventive coatings that use hot water soluble grades of PVA. A preferred grade of PVA for use in the inventive coating is a grade in the medium range (i.e., the grades of PVA between the grades that dissolve only in hot water and the grades that dissolve very easily in cold water) of PVA because the step of heating the water of the liquid coating dispersion may not be necessary, while still maintaining excellent moisture barrier properties in the inventive coating.

The flow aid may be talc, fumed silica, lactose or starch.

The colorant may be any food approved colors, opacifiers, or dyes. For example, these may be aluminum lakes, iron oxides, titanium dioxide, or natural colors.

The soya lecithin, which may be ALCOLEC soya lecithin made by American Lecithin Company, for example, acts an a anti-tack agent, and surprisingly, and unexpectantly, acts as a plasticizer by locking moisture in the coating so the coating stays flexible and not brittle. Surprisingly and unexpectantly, this locked-in moisture in the coating, while contributing to plasticization, does not compromise the moisture barrier properties of the overall coating.

The suspending agent acts as a viscosity modifier stabilizing the coating dispersion. A preferred suspending agent is xanthan gum. Examples of alternative suitable suspending agents include hydroxypropylmethlycellulose (HPMC), alginates, hydroxypropyl cellulose (HPC), natural gums, and carboxymethylcellulose.

The ranges for each component of the dry coating compositions of the invention are as follows, by weight:

|  | Acceptable Ranges | Preferred Ranges |
|---|---|---|
| Polyvinyl Alcohol | 20.0% to 99.8% | 30 to 99.0% |
| Flow Aid | 0.0% to 40.0% | 14.0 to 25.0% |
| Colorant | 0.0% to 60.0% | 25.0 to 40.0% |
| Soya Lecithin | 0.2% to 10.0% | 1.0 to 6.0% |
| Suspending Agent | 0.0% to 2.0% | 0.15 to 1.0% |

The ranges for each component of the liquid coating dispersions of the invention are as follows, by weight:

|  | Acceptable Ranges | Preferred Ranges |
|---|---|---|
| Polyvinyl Alcohol | 5.0 to 40.0% | 7.0 to 12.0% |
| Flow Aid | 0.0 to 16.0% | 3.0 to 5.0% |
| Colorant | 0.0 to 24.0% | 4.8 to 8.0% |
| Soya Lecithin | 0.04 to 4.0% | 0.3 to 0.5% |
| Suspending Agent | 0.0 to 0.8% | 0.07 to 0.12% |
| Water | 60.0 to 95.0% | 75.0 to 85.0% |

DETAILED DESCRIPTION

We now turn to the examples of the invention, all ingredients being by weight.

EXAMPLE 1

455.2 grams of polyvinyl alcohol, 200.0 grams of talc, 320.0 grams of titanium dioxide, 4.8 grams of xanthan gum, and 20.0 grams of soya lecithin are loaded into a dry powder mill, such as a PK blender, and vigorously mixed therein for 25 minutes or until a homogenous mix is achieved, resulting in one formulation of the inventive dry powder moisture barrier film coating composition.

480 grams of this formulation of the inventive dry powder moisture barrier film coating composition is dispersed in 1701.8 grams of purified water to form an aqueous suspension of the invention. Specifically, 1701.8 grams of purified water at ambient temperature is loaded into a vessel having a diameter that is approximately equal to the depth of the final suspension. A low shear mixer, preferably having a mixing head that has a diameter that is approximately ⅓ the diameter of the mixing vessel, is lowered into the water and turned on to create a vortex from the edge of the vessel down to just above the mixing head without any air being drawn into the water. Then, the 480.0 grams of the moisture barrier film coating powder composition is added to the vortex at a rate where there is no excessive build up of dry powder. The speed or depth of the mixing head is adjusted to avoid air being drawn into the suspension so as to avoid foaming. The suspension is stirred for 45 minutes and is then ready for spraying onto substrates like pharmaceutical tablets.

In this Example 1, 10 Kg of tablets are coated with the coating of the invention so as to obtain about a 4.0% weight gain. The extra 80 grams of the dry powder moisture barrier film coating composition above the 400 grams of the dry powder moisture barrier film coating composition needed to obtain a 4.0% weight gain on the tablets is included to allow for losses of coating composition during the coating procedure. 10 Kg of tablets which have logos embossed therein are loaded into a Manesty Model 10 Accela-Cota coater, and the tablets are rotated in the coater at a rotation speed of 12 rpm. The tablets are sprayed with the coating suspension of this Example 1 while the tablets are being rotated. Hot air at 60° C. is used to evaporate the water in sprayed coating suspension and to maintain the tablets at 38° C.

Upon completion of the coating process, the tablets show a smooth surface with excellent logo definition.

In the following Examples 2 to 14, one Kg batches of coating suspension are produced by mixing 220 grams of inventive dry powder moisture barrier coating composition into 780 grams of purified water. These coating suspensions are then sprayed onto tablets. The procedures set out in Example 1 for making the dry powder moisture barrier coating composition, for making the coating suspension, and for spraying the coating suspension onto tablets are used in Examples 2 to 14. The coated tablets of the Examples 2 to 14 show a smooth surface with excellent logo definition.

EXAMPLE 2

| COMPONENT | PERCENTAGE | GRAMS |
|---|---|---|
| PVA | 45.85 | 458.50 |
| TALC | 20.00 | 200.00 |
| TITANIUM DIOXIDE | 32.00 | 320.00 |
| XANTHAN GUM | 0.15 | 1.50 |
| SOYA LECITHIN | 2.00 | 20.00 |
|  | 100.00 | 1000.00 |

EXAMPLE 3

| COMPONENT | PERCENTAGE | GRAMS |
|---|---|---|
| PVA | 44.80 | 448.00 |
| TALC | 20.00 | 200.00 |
| TITANIUM DIOXIDE | 32.00 | 320.00 |
| XANTHAN GUM | 1.20 | 12.00 |
| SOYA LECITHIN | 2.00 | 20.00 |
|  | 100.00 | 1000.00 |

EXAMPLE 4

| COMPONENT | PERCENTAGE | GRAMS |
|---|---|---|
| PVA | 46.52 | 465.20 |
| TALC | 20.00 | 200.00 |
| TITANIUM DIOXIDE | 32.00 | 320.00 |
| XANTHAN GUM | 0.48 | 4.80 |
| SOYA LECITHIN | 1.00 | 10.00 |
|  | 100.00 | 1000.00 |

EXAMPLE 5

| COMPONENT | PERCENTAGE | GRAMS |
|---|---|---|
| PVA | 41.52 | 415.20 |
| TALC | 20.00 | 200.00 |
| TITANIUM DIOXIDE | 18.00 | 180.00 |
| YELLOW IRON OXIDE | 14.00 | 140.00 |
| XANTHAN GUM | 0.48 | 4.80 |
| SOYA LECITHIN | 6.00 | 60.00 |
|  | 100.00 | 1000.00 |

EXAMPLE 6

| COMPONENT | PERCENTAGE | GRAMS |
|---|---|---|
| PVA | 31.64 | 316.40 |
| TALC | 34.09 | 340.90 |
| TITANIUM DIOXIDE | 32.00 | 320.00 |
| XANTHAN GUM | 1.13 | 11.30 |
| SOYA LECITHIN | 1.14 | 11.40 |
| | 100.00 | 1000.00 |

EXAMPLE 7

| COMPONENT | PERCENTAGE | GRAMS |
|---|---|---|
| PVA | 50.40 | 504.00 |
| TALC | 14.40 | 144.00 |
| TITANIUM DIOXIDE | 32.00 | 320.00 |
| XANTHAN GUM | 1.20 | 10.00 |
| SOYA LECITHIN | 2.00 | 20.00 |
| | 100.00 | 1000.00 |

EXAMPLE 8

| COMPONENT | PERCENTAGE | GRAMS |
|---|---|---|
| PVA | 99.00 | 990.00 |
| SOYA LECITHIN | 1.00 | 10.00 |
| | 100.00 | 1000.00 |

EXAMPLE 9

| COMPONENT | PERCENTAGE | GRAMS |
|---|---|---|
| PVA | 99.80 | 998.00 |
| SOYA LECITHIN | 0.20 | 2.00 |
| | 100.00 | 1000.00 |

EXAMPLE 10

| COMPONENT | PERCENTAGE | GRAMS |
|---|---|---|
| PVA | 44.00 | 440.00 |
| TALC | 20.00 | 200.00 |
| TITANIUM DIOXIDE | 18.00 | 180.00 |
| TARTRAZINE ALUMINUM LAKE | 14.00 | 140.00 |
| XANTHAN GUM | 2.00 | 20.00 |
| SOYA LECITHIN | 2.00 | 20.00 |
| | 100.00 | 1000.00 |

EXAMPLE 11

| COMPONENT | PERCENTAGE | GRAMS |
|---|---|---|
| PVA | 50.80 | 508.00 |
| TALC | 14.00 | 140.00 |
| TITANIUM DIOXIDE | 32.00 | 320.00 |
| XANTHAN GUM | 1.20 | 12.00 |
| SOYA LECITHIN | 2.00 | 20.00 |
| | 100.00 | 1000.00 |

EXAMPLE 12

| COMPONENT | PERCENTAGE | GRAMS |
|---|---|---|
| PVA | 40.52 | 405.20 |
| TALC | 25.00 | 250.00 |
| TITANIUM DIOXIDE | 32.00 | 320.00 |
| XANTHAN GUM | 0.48 | 4.80 |
| SOYA LECITHIN | 2.00 | 20.00 |
| | 100.00 | 1000.00 |

EXAMPLE 13

| COMPONENT | PERCENTAGE | GRAMS |
|---|---|---|
| PVA | 25.52 | 255.20 |
| TALC | 40.00 | 400.00 |
| TITANIUM DIOXIDE | 32.00 | 320.00 |
| XANTHAN GUM | 0.48 | 4.80 |
| SOYA LECITHIN | 2.00 | 20.00 |
| | 100.00 | 1000.00 |

EXAMPLE 14

| COMPONENT | PERCENTAGE | GRAMS |
|---|---|---|
| PVA | 45.52 | 455.20 |
| TALC | 20.00 | 200.00 |
| TITANIUM DIOXIDE | 32.00 | 320.00 |
| XANTHAN GUM | 0.48 | 4.80 |
| SOYA LECITHIN | 2.00 | 20.00 |
| | 100.00 | 1000.00 |

EXAMPLE 15

| COMPONENT | GRAMS |
|---|---|
| WATER | 1170.00 |
| PVA | 150.00 |
| TALC | 66.00 |
| TITANIUM DIOXIDE | 105.75 |
| XANTHAN GUM | 1.65 |
| SOYA LECITHIN | 6.60 |
| | 1500.00 |

The coating dispersion of this Example 15 is made and used using the procedures set out in Example 1.

It was unexpectedly found that soya lecithin, included for its tack reduction properties, acts as a plasticizer by locking moisture in the coating so as to keep the coating flexible and not brittle. It is also considered unexpected that this moisture while contributing to plasticization, does not compromise the moisture barrier properties of the overall coating.

This invention provides the means of preparing a moisture barrier coating for application to pharmaceutical solid dosage forms in which the coating composition material is presented as a dry particle powder or granular powder which is readily dispersible in cold water. The resultant coating solution or dispersion is ready to use by applying it to tablets within 45 minutes. The coating solution or dispersion may also be presented in the form of a ready-to-use liquid, or liquid concentrate which is diluted prior to use.

Compared with existing moisture barrier coatings using water insoluble polymers, there is negligible effect on the disintegration time of the coated dosage forms coated with the inventive coating.

The dry form of the invention is manufactured using rotary mixers or mills. The ingredients are loaded and then milled until a homogenous mix is produced. In the case of liquid dispersions, the ingredients are dispersed into hot or cold water and stirred or milled until a homogenous dispersion or solution of the desired correct viscosity is produced.

The dry form of the invention, which comprises a powder of PVA and soya lecithin, and optionally a flow aid, a colorant, and a suspending agent, is dispersed in water and stirred until the PVA is hydrated and a homogenous mixture is produced. The liquid solution or dispersion formed, which comprises PVA, soya lecithin, and any optional components mixed into water, may be ready-to-use or require simple dilution with water prior to use. The resulting coating dispersion is sprayed onto the dosage forms using airless or airborne methods. The movement of air around or through the tablet bed facilitates drying of the film on the tablet surface.

I claim:

1. A liquid moisture barrier film coating composition for forming a moisture barrier film coating for pharmaceutical tablets comprising
    polyvinyl alcohol,
    soya lecithin,
    water, and
    a viscosity modifier,
    the viscosity modifier being xanthan gum, hydroxypropyl-methylcellulose, alginate, hydroxypropyl cellulose, natural gums, carboxymethylcellulose, or combinations thereof.

2. A liquid moisture barrier film coating composition for forming a moisture barrier film coating for pharmaceutical tablets comprising
    polyvinyl alcohol,
    soya lecithin, and
    water,
    the water being in a range of about 60.0% to about 95.0% by weight of the composition.

3. The liquid composition of claim 2,
    the water being in a range of about 75.0% to about 85.0% by weight of the composition.

4. A pharmaceutical tablet coated with a moisture barrier film coating made using a dry moisture barrier film coating composition for forming a moisture barrier film coating for pharmaceutical tablets comprising polyvinyl alcohol, a flow aid, a colorant, a viscosity modifier, and soya lecithin.

5. A dry moisture barrier film coating composition for forming a moisture barrier film coating for pharmaceutical tablets comprising
    polyvinyl alcohol, and
    soya lecithin
    the polyvinyl alcohol being in a range of about 20.0% to about 99.8% by weight of the composition, and
    the soya lecithin being in a range of about 0.2% to about 10.0% by weight of the composition.

6. The coating composition of claim 5,
    the polyvinyl alcohol being in a range of about 30.0% to about 99.0% by weight of the composition, and
    the soya lecithin being in a range of about 1.0% to about 6.0% by weight of the composition.

7. A dry moisture barrier film coating composition for forming a moisture barrier film coating for pharmaceutical tablets comprising
    polyvinyl alcohol,
    soya lecithin, and
    a flow aid
    the flow aid being in a range of greater than 0.0% to about 40.0% by weight of the composition.

8. The composition of claim 7,
    the flow aid being in a range of about 14.0% to about 25% by weight of the composition.

9. A dry moisture barrier film coating composition for forming a moisture barrier film coating for pharmaceutical tablets comprising
    polyvinyl alcohol,
    soya lecithin, and
    a flow aid,
    the flow aid being talc, fumed silica, lactose, or starch.

10. A dry moisture barrier film coating composition for forming a moisture barrier film coating for pharmaceutical tablets comprising
    polyvinyl alcohol,
    soya lecithin, and
    a colorant,
    the colorant being in a range of greater than 0.0% to about 60.0% by weight of the composition.

11. The coating composition of claim 10,
    the colorant being in a range of about 25.0% to about 40.0% by weight of the composition.

12. A dry moisture barrier film coating composition for forming a moisture barrier film coating for pharmaceutical tablets comprising
    polyvinyl alcohol,
    soya lecithin, and
    a colorant,
    the colorant being any food approved colors, opacifiers or dyes.

13. A dry moisture barrier film coating composition for forming a moisture barrier film coating for pharmaceutical tablets comprising
    polyvinyl alcohol,
    soya lecithin, and
    a viscosity modifier,
    the viscosity modifier being in a range of greater than 0.0% to about 2.0% by weight of the composition.

14. The coating composition of claim 13,
    the viscosity modifier being in a range of about 0.15% to about 1.0% by weight of the composition.

15. A dry moisture barrier film coating composition for forming a moisture barrier film coating for pharmaceutical tablets comprising polyvinyl alcohol, soya lecithin, and a viscosity modifier, the viscosity modifier being a xanthan gum.

16. A dry moisture barrier film coating composition for forming a moisture barrier film coating for pharmaceutical tablets comprising polyvinyl alcohol, soya lecithin, and a viscosity modifier, the viscosity modifier being hydroxypropyl-methylcellulose, alginate, hydroxypropyl cellulose, natural gums, carboxymethylcellulose, or combinations thereof.

17. The coating composition of claim 6, the soya lecithin being in a range of about 1.0% further including a flow aid, the flow aid being in a range of about 14% to about 25% by weight of the composition, the flow aid being talc, fumed silica, lactose, or starch, a colorant, the colorant being in a range of about 25.0% to about 40.0% by weight of the composition, the colorant being any food approved colors, opacifiers, or dyes, a viscosity modifier, the viscosity modifier being in a range of about 0.15% to about 1.0% by weight of the composition, the viscosity modifier being xanthan gum, hydroxypropyl-methylcellulose, alginate, hydroxypropyl cellulose, natural gums, carboxymethylcellulose, or combinations thereof.

18. A method of coating substrates with a moisture barrier film coating, comprising mixing the coating composition according to claim 5 into water to form an aqueous coating solution/dispersion, applying the coating solution/suspension onto the substrates to form a film coating on the substrates, and drying the film coating on said substrates.

19. A pharmaceutical tablet coated with a moisture barrier film coating made using the coating composition according to claim 17.

20. A method of coating substrates with a moisture barrier film coating, comprising mixing the coating composition according to claim 17 into water to form an aqueous coating solution/dispersion, applying the coating solution/suspension onto the substrates to form a film coating on the substrates, and drying the film coating on said substrates.

21. A dry moisture barrier film coating composition for forming a moisture barrier film coating for pharmaceutical tablets comprising polyvinyl alcohol, and soya lecithin, the polyvinyl alcohol being in a range of about 20.0% to about 99.8% by weight of the composition.

22. A dry moisture barrier film coating composition for forming a moisture barrier film coating for pharmaceutical tablets comprising polyvinyl alcohol, and soya lecithin, the soya lecithin being in a range of about 0.2% to about 10.0% by weight of the composition.

23. A coated substrate made in accordance with the method of claim 18.

24. A liquid moisture barrier film coating composition for forming a moisture barrier film coating for pharmaceutical tablets comprising polyvinyl alcohol, soya lecithin, and water, the polyvinyl alcohol being in a range of about 5.0% to about 40.0% by weight of the composition, and the soya lecithin being in a range of about 0.04% to about 4.0% by weight of the composition.

25. The liquid composition of claim 24, the polyvinyl alcohol being in a range of about 7.0% to about 12.0% by weight of the composition, and the soya lecithin being in a range of about 0.3% to about 0.5% by weight of the composition.

26. A liquid moisture barrier film coating composition for forming a moisture barrier film coating for pharmaceutical tablets comprising polyvinyl alcohol, soya lecithin, water, and a flow aid, the flow aid being in a range of greater than 0.0% to about 16.0% by weight of the composition.

27. The liquid composition of claim 26, the flow aid being in a range of about 3.0% to about 5.0% by weight of the composition.

28. A liquid moisture barrier film coating composition for forming a moisture barrier film coating for pharmaceutical tablets comprising polyvinyl alcohol, soya lecithin, water, and a flow aid, the flow aid being talc, fumed silica, lactose, or starch.

29. A liquid moisture barrier film coating composition for forming a moisture barrier film coating for pharmaceutical tablets comprising polyvinyl alcohol, soya lecithin, water, and a colorant, the colorant being in a range of greater than 0.0% to about 24.0% by weight of the composition.

30. The liquid composition of claim 29, the colorant being in a range of about 4.8% to about 8.0% by weight of the composition.

31. A liquid moisture barrier film coating composition for forming a moisture barrier film coating for pharmaceutical tablets comprising polyvinyl alcohol, soya lecithin, water, and a colorant, the colorant being any food approved colors, opacifiers or dyes.

32. A liquid moisture barrier film coating composition for forming a moisture barrier film coating for pharmaceutical tablets comprising
polyvinyl alcohol,
soya lecithin,
water, and
a viscosity modifier,
the viscosity modifier being in a range of greater than 0.0% to about 0.8% by weight of the composition.

33. The liquid composition of claim 32,
the viscosity modifier being in a range of about 0.07% to about 0.12% by weight of the composition.

* * * * *